United States Patent [19]

Boltze

[11] Patent Number: 4,459,415

[45] Date of Patent: Jul. 10, 1984

[54] PROCESS FOR THE PREPARATION OF 1-(4-CHLOROBENZOYL)-5-METHOXY-2-METHYL-3-INDOLEACETOXYACETIC ACID

[75] Inventor: Karl-Heinz Boltze, Borod, Fed. Rep. of Germany

[73] Assignee: Troponwerke GmbH & Co. KG, Cologne, Fed. Rep. of Germany

[21] Appl. No.: 469,672

[22] Filed: Feb. 25, 1983

[30] Foreign Application Priority Data

Feb. 26, 1982 [DE] Fed. Rep. of Germany ....... 3206888

[51] Int. Cl.$^3$ ............................................ C07D 209/28
[52] U.S. Cl. ...................................... 548/501; 548/500
[58] Field of Search ................................ 548/501, 500

[56] References Cited

FOREIGN PATENT DOCUMENTS 2234651  4/1974  Fed. Rep. of Germany .
1411350 10/1975  United Kingdom .

OTHER PUBLICATIONS

Fisnerova et al., Chem. Abstracts, 90: 87267x, (1979).

Primary Examiner—Paul M. Coughlan, Jr.
Assistant Examiner—D. B. Springer
Attorney, Agent, or Firm—Sprung, Horn, Kramer & Woods

[57] ABSTRACT

The invention relates to a process for the preparation of the known 1-(4-chlorobenzoyl)-5-methoxy-2-methyl-3-indoleacetoxyacetic acid which comprises reacting an indolecarboxylic acid ester of Formula (II) or its derivative with an alcohol of Formula (III). The final product is known to have antiinflammatory activity.

7 Claims, No Drawings

PROCESS FOR THE PREPARATION OF 1-(4-CHLOROBENZOYL)-5-METHOXY-2-METHYL-3-INDOLEACETOXYACETIC ACID

The present invention relates to a new process, which is chemically original and advantageous, for the preparation of the known 1-(4-chlorobenzoyl)-5-methoxy-2-methyl-3-indoleacetoxyacetic acid (designated I in the following text).

A number of processes have already been disclosed for the preparation of this known compound, compare, for example, DE-OS (German Published Specification) No. 2,234,651, DE-OS (German Published Specification) No. 2,257,867 and DE-OS (German Published Specification) No. 2,943,125.

In the known processes, the carboxyl group is initially protected by a benzyl radical, so that catalytic hydrogenation of the benzyl ester in accordance with the reaction scheme below must be carried out in a final reaction step.

Reaction scheme

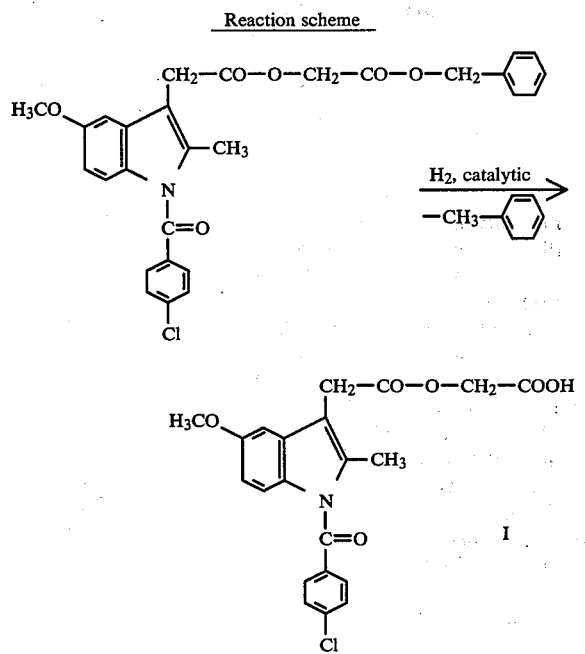

During this removal of the benzyl radical, 1-benzoyl-5-methoxy-2-methyl-3-indoleacetoxyacetic acid, called the dechlorinated compound in the following text, is always produced as a by-product. This undesired impurity, which arises in an amount up to 0.5% by removal of the chlorine from the benzene ring of the 4-chlorobenzoyl radical, must subsequently be removed in elaborate purification steps, and this is associated with losses in yield.

The object of the present invention is to provide an alternative preparation process in which the undesired dechlorinated compound is not produced.

It has been found, surprisingly, that 1-(4-chlorobenzoyl)-5-methoxy-2-methyl-3-indoleacetoxyacetic acid I is obtained in a simple manner and in high purity when indolecarboxylic acid or its derivatives of the general formula II

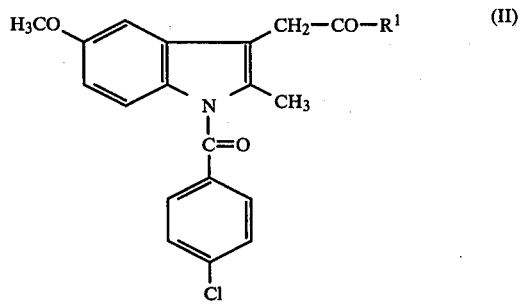

in which $R^1$ represents one of the radicals

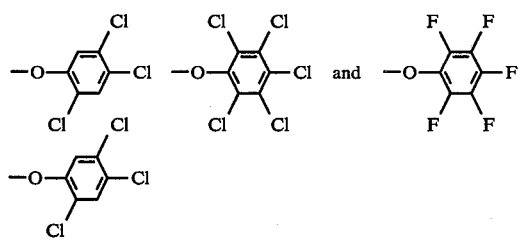

and preferably is reacted with compounds of the general formula III

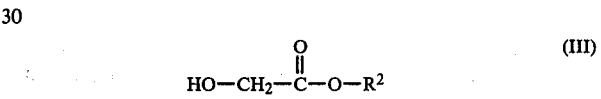

in which $R^2$ represents hydrogen or ammonium, in the presence of inert organic solvents, such as, for example, ethers, diethyl ether, diisopropyl ether, dioxane, tetrahydrofuran, 1,2-dimethoxyethane, chlorinated hydrocarbons, methylene chloride, chloroform, dichloroethane, substituted amides, dimethylformamide, N-methylpyrroliddone, aromatics, toluene, xylene, ketones, acetone, methyl ethyl ketone (2-butanone) in a temperature range from $-10°$ C. to $80°$ C., preferably at $-10°$ to $50°$ C., particularly preferably at $-5°$ C. to $20°$ C.

If, as a representative of the general formula II, the indolecarboxylic acid derivatives, in which $R^1$ denotes the abovementioned substituents, and compounds of the general formula III are used as starting materials, the course of the reaction can be represented by the following reaction scheme:

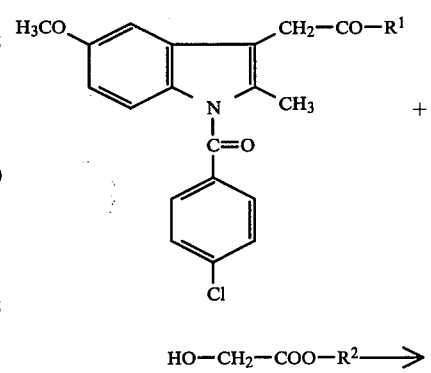

-continued

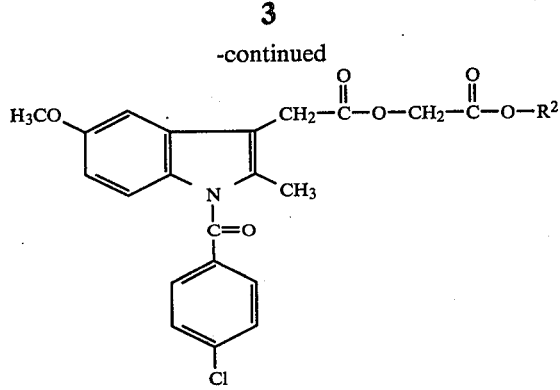

$R^1$ in this instance preferably represents

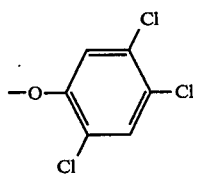

$R^2$ preferably represents an ammonium cation.

The ammonium compounds produced are subsequently converted into the final product I in a simple manner by treatment with acids.

It was surprising that 1-(4-chlorobenzoyl)-5-methoxy-2-methyl-3-indoleacetoxyacetic acid is produced by these processes in such a pure form, that is to say free of the interfering dechlorinated compound, and in yields of 60–70% of theory.

The compounds of the formula II and III used as starting materials are known or are prepared by known processes.

The final compound I prepared by the processes according to the invention is a valuable pharmaceutical active substance having an antiinflammatory effect, compare, for example, German Patent Specification No. 2,234,651.

In the present process, the indolecarboxylic acid II ($R^1$=OH) is functionalised by formation of esters with various halogen-substituted phenols. The 2,4,5-trichlorophenyl, 2,3,4,5,6-pentachlorophenyl and 2,3,4,5,6-pentafluorophenyl esters are used for this purpose, but preferably the 2,4,5-trichlorophenyl ester. The esters prepared as intermediate compounds are very reactive towards protonic reagents. Under certain conditions, they can be isolated and prepared pure; it is also possible to prepare them as active esters and to react them further in the same batch by immediate nucleophilic attack.

The active esters which are sensitive to moisture, must be worked within absolute aprotic solvents, such as ether, diisopropyl ether, dioxane, tetrahydrofuran, methylene chloride or dimethylformamide (DMF), DMSO and N-methylpyrrolidone; methylene chloride is preferred.

If indolecarboxylic acid and phenols in the free form are brought to reaction, the use of a condensation agent, for example dicyclohexylcarbodiimide in this case, is necessaary; the acid chloride of the indolecarboxylic acid can also be employed, with or without a base, for example triethylamine, pyridine or potassium carbonate or sodium carbonate.

The reaction temperatures are between −10° and +50° C.; −10° to −5° C. and 20° C. are preferred.

In the reaction of the active esters with the bifunctional glycolic acid, many compounds are obtained, which are difficult to separate. Only the use of ammonium salts of glycolic acid, in particular its triethylammonium or diisopropylammonium salt, lead to good yields and high purity of the desired compounds.

A further advantage of these salts of I, in particular of the diisopropylammonium salt, lies in the possibility of carrying out the final purification with them up to the high standard which is required of a pharmaceutical product.

The reactions must be carried out with exclusion of moisture in absolute aprotonic solvents, such as ether, diisopropyl ether, dioxane, tetrahydrofuran, 1,2-dimethoxyethane or dimethylformamide, the latter being preferred.

The reaction temperatures are between 10°–80° C., 20° C. and 60° C. being preferred.

In order to convert the purified ammonium salts into the free indolecarboxylic acid I, treatment with hydrochloric acid is subsequently carried out, the reactions and crystallisation being carried out such that the hydrate of I is obtained as colourless crystals in a defined form. The subsequent drying in vacuo at 90° provides yellowish crystals of I, with complete removal of water. In an analogous reaction procedure, I is obtained from the 2,3,4,5,6-pentachloro and 2,3,4,5,6,-pentafluorophenyl esters of II.

3. Reaction scheme: Synthesis of I by the active ester process
(Steps a–d)

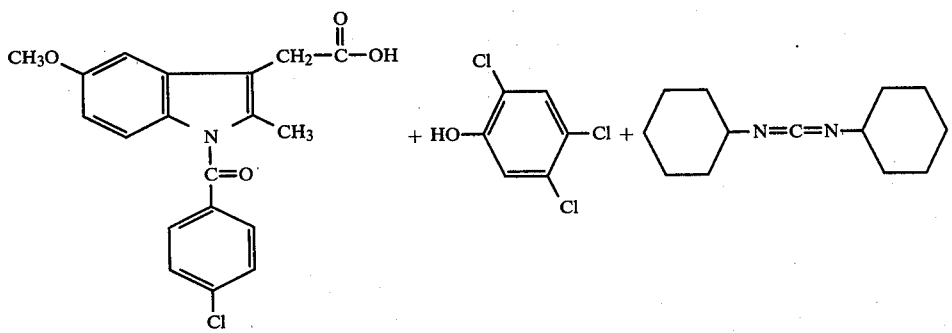

(a)

3. Reaction scheme: Synthesis of I by the active ester process
(Steps a-d)
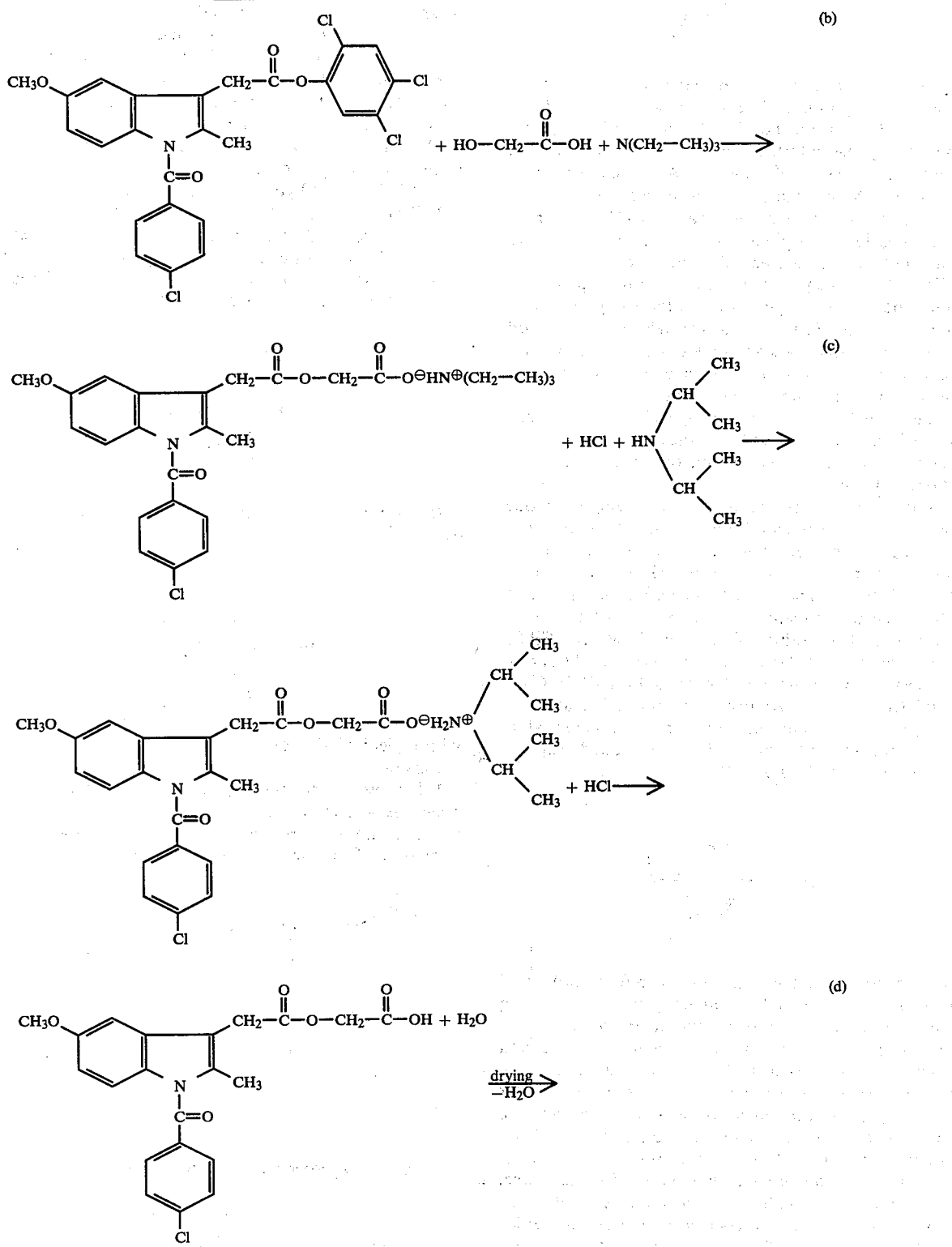
EXAMPLE 1
(a) 2,4,5-Trichlorophenyl ester

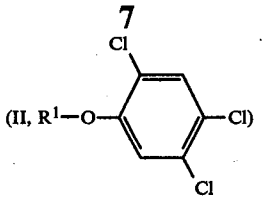

24.8 g of dicyclohexylcarbodiimide (0.12 mol) are added to a solution of 43.2 g of II (R¹OH) and 26.04 g of 2,4,5,-trichlorophenol (0.132 mol) in 700 ml of absolute methylene chloride, cooled to −10° C., with stirring and exclusion of moisture. After removal of the cooling bath, the temperature of the reaction mixture is allowed to rise to room temperature within 1 hour and the colourless crystalline solid material, which has precipitated out, is filtered off. The filtrate is freed of CH₂Cl₂ in a rotary evaporator under a waterpump vacuum and 400 ml of petroleum ether are added to the yellow syrupy residue. The crystals which are produced by seeding and scratching are filtered off with suction, washed with petroleum ether and dried in a desiccator under waterpump vacuum.

Yield: 64.4 g of 2,4,5-trichlorophenyl 1-(4-chlorobenzoyl)-5-methoxy-2-methyl-3-indoleacetoxyacetate=100% of theory; melting point: 126.2° C. (Mettler FP 61).

The following are prepared in an analogous procedure: 2,3,4,5,6-pentachlorophenyl 1-(4-chlorobenzoyl)-5-methoxy-2-methyl-3-indoleacetoxyacetate with a melting point: 161.7° C. (Mettler FP 61) in a yield of 85% of theory and 2,3,4,5,6-pentafluorophenyl 1-(4-chlorobenzoyl)-5-methoxy-2-methyl-3-indoleacetoxyacetate with a melting point: 131.6° C. (Mettler FP 61) in a yield of about 100% of theory; (compare literature: J. Pless, R. A. Boissonnas, Helvitica 46, 1609 (1963).

(b) Reaction with triethylammonium glycolate.

(c) Conversion into the diisopropylammonium salt of I 4.15 ml of triethylamine (0.03 mol) are added dropwise to a solution of 10.74 g of II

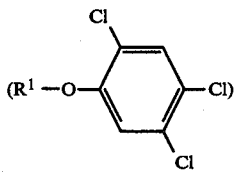

(0.,02 mol) and 2.28 g of glycolic acid (0.03 mol) in 50 ml of absolute dimethylformamide (DMF), with stirring and exclusion of moisture at room temperature and the mixture is stirred for a further 18 hours. The reaction solution is then heated at 60° C. for 2½ hours and the solvent is then distilled off in a rotary evaporator under waterpump vacuum. 80 ml of methylene chloride are then added to the syrupy residue. 25 ml of 1N HCl are added to the methylene chloride solution and this is then washed three times with 50 ml of H₂O each time. After drying the methylene chloride phase with Na₂SO₄, 2.8 ml of diisopropylamine (0.02 mol) are added to the solution and CH₂Cl₂ is distilled off in a rotary evaporator. The residue is taken up in 80 ml of ether and, after seeding and stirring (1 hour at room temperature), the colourless crystalline substance is filtered off with suction, washed with ether and dried in a desiccator at 40° C.

Yield: 8.2 g of diisopropylammonium 1-(4-chlorobenzoyl)-5-methoxy-2-methyl-3-indoleacetoxyacetate (d) Conversion into I.

8.2 g of the ammonium salt thus obtained are dissolved in 32 ml of acetone and 10.5 ml of H₂O with stirring. 6 ml of 1N HCl are then added to the solution and it is seeded. 10 ml of 1N HCl are added dropwise within 1 hour and the mixture is subsequently stirred for 1 hour until crystallisation is complete. The colourless crystalline substance is filtered off with suction, thoroughly washed with H₂O and dried in a desiccator under waterpump vacuum at 40° C.

Yield: 5.3 g of I hydrate=61% of theory;

Yellowish crystals of I, which melt at 151°–152° C., are produced by drying under waterpump vacuum at 90° C. (1 hour) with complete removal of water.

In an analogous procedure, I is prepared via synthesis steps b–d, both from the active ester II

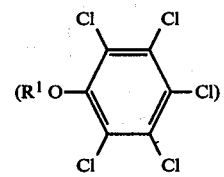

with a yield of 42% of theory and also from the active ester II

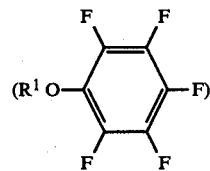

with a yield of 55% of theory.

I claim:

1. Process for the preparation of 1-(4-chlorobenzoyl)-5-methoxy-2-methyl-3-indoleacetoxyacetic acid (I), which comprises reacting indolecarboxylic acid or a derivative of the formula II

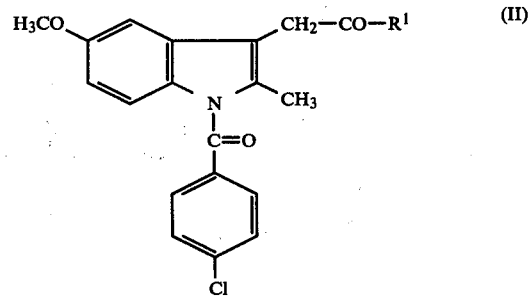

in which R¹ represents one of the radicals

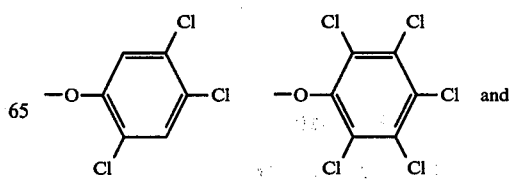

-continued

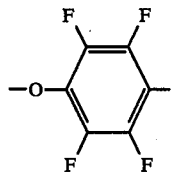

with a compound of the formula III

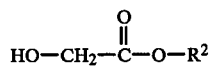

in which $R^2$ represents hydrogen or ammonium, in the presence of an inert organic solvent in a temperature range from $-10°$ C. to $80°$ C.

2. Process according to claim 1, wherein the reaction is undertaken in a temperature range from $-10°$ C. to $80°$ C.

3. Process according to claim 2 wherein the reaction is undertaken in a temperature range from $-5°$ C. to $20°$ C.

4. Process according to claim 1, where an ether, a chlorinated hydrocarbon, a substituted amide, an aromatic hydrocarbon or a ketone is employed as the inert organic solvent.

5. Process according to claim 4, wherein diethyl ether, diisopropyl ether, dioxane, tetrahydrofuran, 1,2-dimethoxyethane; mthylene chloride, chloroform, dichloroethane; dimethylformamide, N-methylpyrrolidone; toluene, xylene, acetone and/or methyl ethyl ketone (2-butanone) is employed as the inert organic solvent.

6. Process according to claim 1 characterized in that $R^1$ denotes

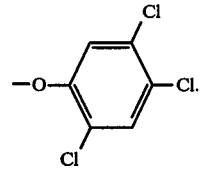

7. Process according to claim 1 characterized in that $R^2$ denotes ammonium.

* * * * *